United States Patent [19]

Correia et al.

[11] Patent Number: 5,278,122
[45] Date of Patent: Jan. 11, 1994

[54] CATALYST FOR DEHALOGENATION OF ALPHA-HALOGENATED CARBOXYLIC ACIDS/ESTERS

[75] Inventors: Yves Correia, Chateau-Arnoux; Michel Bertucci, Lyons, both of France

[73] Assignee: Atochem, Puteaux, France

[21] Appl. No.: 969,393

[22] Filed: Oct. 30, 1992

Related U.S. Application Data

[62] Division of Ser. No. 505,985, Apr. 6, 1990, Pat. No. 5,191,118.

[30] Foreign Application Priority Data

Apr. 7, 1989 [FR] France ................. 89 04607

[51] Int. Cl.$^5$ ............................................. B01J 27/045
[52] U.S. Cl. .................................................... 502/185
[58] Field of Search ................ 502/185, 223; 562/604

[56] References Cited

U.S. PATENT DOCUMENTS

| | | | |
|---|---|---|---|
| 2,671,803 | 3/1954 | Sennewald et al. | 562/604 |
| 2,725,411 | 11/1955 | Ladd et al. | 562/604 X |
| 2,863,917 | 12/1958 | Rucker et al. | 562/604 |
| 3,071,615 | 1/1963 | Opitz et al. | 562/604 |
| 3,226,386 | 12/1965 | Kober | 562/604 X |
| 3,336,386 | 8/1967 | Dovell et al. | 502/223 X |
| 3,652,455 | 3/1972 | Baader et al. | 562/604 X |
| 3,660,306 | 5/1972 | Sennewald et al. | 562/604 X |
| 3,739,023 | 6/1973 | Sennewald et al. | 562/604 |
| 4,236,024 | 11/1980 | Matsuda et al. | 502/223 X |
| 4,288,422 | 9/1981 | Chianelli et al. | 502/223 X |

FOREIGN PATENT DOCUMENTS

| | | |
|---|---|---|
| 555342 | 4/1958 | Canada . |
| 645929 | 7/1962 | Canada . |
| 1959578 | 6/1971 | Fed. Rep. of Germany . |
| 2582645 | 5/1985 | France . |
| 1004345 | 4/1981 | U.S.S.R. . |
| 870040 | 7/1961 | United Kingdom . |
| 1419603 | 11/1973 | United Kingdom . |
| 1411214 | 5/1974 | United Kingdom . |

OTHER PUBLICATIONS

*Alfa Catalog*, Morton Thiokol, Inc., 1986-87, p. 446.
Chem. Abs., 112(14):121827g, 1989.
Chem. Abs., 102(20):173635, 1985.
Journal of Catalysis, vol. 120, No. 2, pp. 473-477, 1989.
"Hydrogenation Methods," P. N. Rylander, Academic Press, London 1985, p. 152.

*Primary Examiner*—W. J. Shine
*Assistant Examiner*—Douglas J. McGinty
*Attorney, Agent, or Firm*—Burns, Doane, Swecker & Mathis

[57] ABSTRACT

The alpha-halogenated carboxylic acids/esters are dehalogenated by reaction with hydrogen in the presence of a catalytically effective amount of (i) a Group VIII precious metal catalyst and (ii) either sulfur or a sulfur compound, or (iii) a novel precious metal/sulfur solid phase catalyst; the subject dehalogenation is especially adapted for enriching the monochloroacetic acid content of MCAA/DCAA mixtures.

6 Claims, No Drawings

CATALYST FOR DEHALOGENATION OF ALPHA-HALOGENATED CARBOXYLIC ACIDS/ESTERS

This application is a divisional of application Ser. No. 07/505,985, filed Apr. 6, 1990, now U.S. Pat. No. 5,191,118.

BACKGROUND OF THE INVENTION

1. Field of the Invention

The present invention relates to the catalytic dehalogenation of alpha-halogenated carboxylic acids, and, more especially, to the selective catalytic dehalogenation of the dichloroacetic acid (DCAA) fraction present in monochloroacetic acid (MCAA).

2. Description of the Prior Art

The synthesis of monochloroacetic acid is carried out on an industrial scale by the chlorination of acetic acid, but dichloroacetic acid and sometimes a minor amount of trichloroacetic acid are also unavoidably formed. Therefore, upon completion of the chlorination reaction, a mixture of monochloroacetic acid, dichloroacetic acid, trichloroacetic acid and unreacted acetic acid is characteristically produced.

Because of the proximity of the boiling points of MCAA (189° C.) and of DCAA (194° C.), it is practically impossible to separate these species by distillation. On the other hand, it is quite simple to hydrogenate such a mixture to convert the DCAA into MCAA according to the reaction:

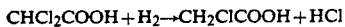

$$CHCl_2COOH + H_2 \rightarrow CH_2ClCOOH + HCl$$

But this hydrogenation is not completely selective and a reversion of MCAA to acetic acid is also observed, as follows:

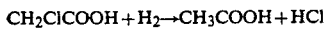

$$CH_2ClCOOH + H_2 \rightarrow CH_3COOH + HCl$$

This reaction is carried out in the presence of a catalyst and also produces acetaldehyde, which has the disadvantage of giving rise to objectionable condensation products.

FR 1,581,391 describes such a process based on a catalyst of silica in the form of cylinders 8 mm in length and 3.5 mm in diameter, which has a palladium content of 0.5% by weight.

FR 2,039,987 describes a process of the same type as the above, but entailing introduction of either salts or oxides of the alkali or alkaline earth metals or of rare earths, or an organic compound designated a protonacceptor, which may be, for example, triethylamine, pyridine, piperidine, glycine, urea, triphenylphosphine, butyraldehyde, diisobutyl ketone, butyl acetate or hydrocyanic acid. This catalyst activator is introduced into the mixture to be hydrogenated and can be recovered by distillation of the hydrogenated mixture. It can be recycled into the mixture to be hydrogenated.

SUMMARY OF THE INVENTION

Accordingly, a major object of the present invention is the provision of an improved process for the catalytic dehalogenation of alpha-halogenated carboxylic acids in the presence of an activator, such catalyst activation being long-lived and even continuing, in modified state, after introduction of the activator into the mixture to be hydrogenated has been terminated.

Another object of the present invention is the provision of an improved process for the selective catalytic hydrogenation of the di- and tri-alpha-halogenated carboxylic acids.

Yet another object of this invention is the provision of an improved process for the catalytic dehalogenation of alpha-halogenated carboxylic acids while minimizing by-production of the corresponding aldehydes.

Another object of this invention is the provision of an improved hydrogenation/dehalogenation catalyst, per se.

Briefly, the present invention features a process for the dehalogenation of alpha-halogenated carboxylic acids, or esters thereof, comprising reacting such acids/esters with hydrogen in the presence of a catalyst based on a precious metal of Group VIII of the Periodic Table, and wherein such catalytic dehalogenation is carried out in the presence of sulfur or a sulfur compound.

DETAILED DESCRIPTION OF THE PREFERRED EMBODIMENTS OF THE INVENTION

More particularly according to the present invention, and while it is applicable to any alpha-halogenated carboxylic acids, the preferred acids have the formula:

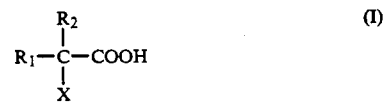

in which X is chlorine or bromine, and $R_1$ and $R_2$, which may be identical or different, are each X, H, a linear or branched chain alkyl radical having from 1 to 12 carbon atoms, or a cycloalkyl radical having from 3 to 12 carbon atoms. The invention is also applicable to the esters of the acids of formula (I); these are preferably aliphatic esters having from 1 to 10 carbon atoms and preferably from 1 to 5 carbon atoms.

According to this invention, the dehalogenation of a single acid or of a mixture of acids may be carried out. These acids may also be in admixture with a solvent.

The precious metals of Group VIII of the Periodic Table include ruthenium, rhodium, palladium, osmium, iridium and platinum. The first three are advantageously employed, and preferably palladium. These metals may be employed by themselves, as alloys, or mixed with each other. They may be employed as such, or deposited onto a support, for example charcoal, silica, silicon carbide or boron carbide.

The catalyst may be employed in the form of fine particles, namely, the acids and the catalyst are mixed, sulfur is added and hydrogen is introduced.

Depending on the end applications for the dehalogenated acids, it is sometimes necessary to separate the catalyst from the acids upon completion of dehalogenation. In a preferred embodiment of the invention, the catalyst is arranged as a stationary bed or as a fluid bed, in a vessel, and the acids to be dehalogenated, the hydrogen and the sulfur are introduced into this vessel. It is therefore not necessary to separate the catalyst upon completion of dehalogenation. A catalyst is preferably employed as a stationary bed and the operation is continuous.

The precious metal is advantageously deposited onto a charcoal having a large surface area, in a proportion of 0.3 to 1% by weight of the catalyst, namely, of the charcoal plus the metal, and it is distributed over the surface of the charcoal. A charcoal having a large surface area is one having a surface area of approximately 600 m²/g and even up to 1,300 m²/g. This charcoal is advantageously in the form of small extruded cylinders or of a powder of approximately 50 μ. The amount of catalyst is easily determined by one skilled in this art.

Sulfur or sulfur compounds are advantageously added into the acids to be dehalogenated. Exemplary sulfur compounds are $SCl_2$, $S_2Cl_2$, $CS_2$, thiophene, or sulfur/oxygen compounds. The sulfur or the sulfur compounds are added in the form of minor amounts of up to 1 g per kg of acid or of the mixture containing the acids to be hydrogenated, and preferably from 0.1 to 200 mg/kg, expressed as sulfur.

It is advantageous to carry out the process of the invention with the acids in liquid phase. Although it is possible to operate at any temperature, it is advantageous to utilize a temperature ranging from that at which the acids are liquid to 200° C., and preferably from 100° to 180° C. If necessary, the acid(s) may be dissolved in a solvent to permit operation within this preferred temperature range.

The process may be carried out at atmospheric pressure or at a pressure of up to 5 bars. The effect of pressure is to increase the reaction kinetics; since the acids are corrosive and also the reaction medium of the invention, it is not judicious to exceed a pressure on the order of 5 bars.

The invention is particularly useful for purifying impure mono-alpha-halogenated carboxylic acids $R_1CHXCOOH$, wherein $R_1$ is as defined above. These acids are prepared by halogenation of the corresponding acid $R_1CH_2COOH$; a mixture of $R_1CHXCOOH$, of $R_1CX_2COOH$, of unconverted acid $R_1CH_2COOH$ is obtained, sometimes including trace amounts of $CX_3COOH$ in the particular case of acetic acid, $CH_3COOH$.

$R_1CH_2COOH$ could first be separated from this mixture, but it is simpler to conduct the hydrogenation:

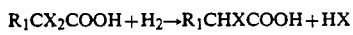
$R_1CX_2COOH + H_2 \rightarrow R_1CHXCOOH + HX$ and then to separate the nonhalogenated acid, since unavoidably a fraction of the $R_1CHXCOOH$ is converted back into such acid according to the reaction scheme:

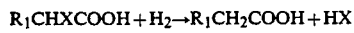
$R_1CHXCOOH + H_2 \rightarrow R_1CH_2COOH + HX$

It then suffices to distill the mixture of $R_1CHXCOOH$, of $R_1CH_2COOH$ and of HX, to obtain relatively pure $R_1CHXCOOH$.

The invention is particularly applicable to the purification of monochloroacetic acid.

The dehalogenation is characteristically commenced with the catalyst alone, without the sulfur values. The sulfur is then introduced and a few hours later, while the sulfur is still being introduced, a slightly lower conversion of $R_1CX_2COOH$ is observed at the same temperature, a much lower reversion and a large decrease in the byproduct aldehyde $R_1CH_2CHO$.

The reversion is the ratio between the number of $X^-$ ions in the purified acid, i.e., those originating from HX to the theoretical number of X to be removed from $R_1CX_2COOH$ (and possibly $CX_3COOH$) to convert it into $R_1CHXCOOH$. With the exception of $CX_3COOH$, the minimum reversion is 1. This reversion in most cases ranges from 1.4 to 3.4.

Unexpectedly, it has now surprisingly been found that when the introduction of sulfur is terminated, its effects continued in a relatively unmodified form, namely, the conversion of $R_1CX_2COOH$ increases again and exceeds that of the prior art, the reversion increases again and ranges from the above value to that of the prior art, the aldehyde level increases again and is also situated between the above value and that of the prior art.

The process can be continued while resuming the introduction of the sulfur (which had been terminated); a return to the values observed during the initial introduction of the sulfur is determined.

It has also been determined that the catalyst based on a precious metal was converted into a catalyst based on a solid phase of sulfur and of the precious metal. Thus, the present invention also features such novel catalyst, per se. This catalyst is advantageously a solid phase of sulfur and of palladium deposited onto a support which may be charcoal, silica, silicon carbide or boron carbide.

This catalyst is preferably $Pd_4S$ deposited onto charcoal.

The present invention also features a process for the dehalogenation of alpha-halogenated carboxylic acids, or esters thereof, by reacting such acids/esters with hydrogen in the presence of a catalyst comprising a solid phase of sulfur and of a precious metal of Group VIII.

In this process employing such solid phase, it is also possible to continue to add the sulfur, advantageously in the feedstream of the acids to be dehalogenated. At the outlet of the reactor, the sulfur is recovered in the dehalogenated acids in the form of compounds which can be removed by distillation. The operating conditions are the same as those described above. This process employing the catalyst which is a sulfur/precious metal solid phase, in combination with an addition of sulfur or otherwise, can also be used for purifying the acids $R_1CHXCOOH$, and in particular monochloroacetic acid.

In order to further illustrate the present invention and the advantages thereof, the following specific examples are given, it being understood that same are intended only as illustrative and in nowise limitative.

EXAMPLE 1

A jacketed glass column A, 26 mm in internal diameter, was charged with 300 cm³ of an extruded charcoal 2 mm in diameter and 4 mm in length, having a specific surface area > 700 m²/g and containing 0.8% of palladium deposited at the surface (> 100 m²/g of palladium).

This column was then concurrently charged with an acid solution (in % by weight): approximately 80% monochloroacetic acid, approximately 4% dichloroacetic acid, approximately 16% acetic acid, and with a hydrogen stream of 4 normal liters per hour.

The temperature of the column was increased, to 125° C., and after a period of time to equilibrate the reaction conditions, feed changes were carried out and the results reported in Table I were observed.

The column was charged with a liquid containing 30 ppm of sulfur from the 187th hour to the 355th hour.

The results are reported in Table I;

The "hours of operation" denote the cumulative hours from time 0;

LSV denotes the liquid space velocity.

A determination of sulfur in the MCAA at the outlet of the column was made at the 350th hour; 29 ppm were found.

X-ray diffraction analysis of catalyst granules removed after the 350th hour evidenced the presence of Pd$_4$S and the absence of Pd.

TABLE I

| Hours of operation | L.S.V. kg/h m$^3$ | Outlet DCAA % | CH$_3$CHO formed mg/kg | Reversion |
|---|---|---|---|---|
| 165 | 245 | 0.12 | 1185 | 3 |
| 187 | 235 | 0.13 | 307 | 1.77 |
| 211 | 234 | 0.22 | 238 | 1.73 |
| 284 | 244 | 0.3 | 242 | 1.87 |
| 355 | 244 | 0.33 | 232 | 1.84 |
| 379 | 243 | 0.25 | 416 | 1.90 |
| 413 | 251 | 0.08 | 656 | 2.30 |
| 442 | 244 | 0.06 | 776 | 2.42 |
| 468 | 244 | 0.08 | 786 | 2.30 |
| 540 | 249 | <0.03 | 982 | 2.14 |
| COLUMN STOPPED | | | | |

EXAMPLE 2

The procedure of Example 1 was repeated with a column B identical with A, but using S$_2$Cl$_2$ (30 ppm as S) between the 353rd hour and the 616th hour. The results are reported in Table II:

TABLE II

| Hours of operation | L.S.V. kg/h m$^3$ | Outlet DCAA % | CH$_3$CHO formed mg/kg | Reversion |
|---|---|---|---|---|
| 165 | 247 | 0.21 | 1513 | 3.05 |
| 189 | 241 | 0.16 | 1371 | 3.09 |
| 252 | 243 | 0.12 | 1366 | 3.37 |
|  |  | 0.16 | 1243 | 3.28 |
| 350 | 249 | 0.07 | 1321 | 2.61 |
| 353 |  |  |  |  |
| 374 | 242 | 0.15 | 323 | 1.5 |
| 422 | 234 | 0.20 | 274 | 1.48 |
| 518 | 233 | 0.20 | 295 | 1.40 |
| 568 | 210 | 0.13 | 287 | 1.44 |
| 616 | 215 | 0.17 | 256 | 1.40 |
| 663 | 246 | 0.14 | 690 | 1.91 |
| 758 | 237 | 0.11 | 938 | 2.28 |

Catalyst granules were removed after the 400th hour and, as in Example 1, only Pd$_4$S was found therein.

EXAMPLE 3

Column A was used as in Example 1 with the catalyst that had been used in Example 1, but between the 685th and 827th hour 36 ppm of carbon sulfide were added to the impure MCAA. The results are reported in Table III:

TABLE III

| Hours of operation | L.S.V. kg/h m$^3$ | Outlet DCAA % | CH$_3$CHO formed mg/kg | Reversion |
|---|---|---|---|---|
| 590 | 247 | <0.03 | 951 | 2.25 |
| 685 | 234 | <0.03 | 1174 | 2.47 |
| 709 | 250 | 0.05 | 307 | 1.56 |
| 755 | 253 | 0.08 | 276 | 1.55 |
| 803 | 236 | 0.06 | 289 | 1.63 |
| 827 | 245 | 0.08 | 247 | 1.63 |

The sulfur determined at the column outlet during the injection of CS$_2$ was approximately 27 mg/kg.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A catalyst comprising a solid palladium phase, Pd$_4$S, deposited onto a charcoal support.

2. The catalyst according to claim 1, wherein the palladium is present in a proportion of 0.3 to 1% by weight of the charcoal plus the metal.

3. The catalyst according to claim 1, wherein the palladium sulfide is distributed over the surface of the charcoal.

4. The catalyst according to claim 1, wherein the charcoal has a surface area of approximately 600 m$^2$/g to 1300 m$^2$/g.

5. The catalyst according to claim 1, wherein the charcoal is in the form of extruded cylinders.

6. The catalyst according to claim 1, wherein the charcoal is in the form of a powder.

* * * * *